United States Patent
Hruschka et al.

(10) Patent No.: US 9,105,366 B2
(45) Date of Patent: Aug. 11, 2015

(54) ARRANGEMENT AND METHOD FOR AN X-RAY IMAGE SYSTEM WITH A GRID FRAME ARRANGED TO ENABLE THE GRID FRAME TO OSCILLATE

(71) Applicants: Klaus Hruschka, Erbendorf (DE); Michael Kleber, Eslarn (DE); Philip Materne, Kulmain (DE); Josef Rupprecht, Erbendorf (DE)

(72) Inventors: Klaus Hruschka, Erbendorf (DE); Michael Kleber, Eslarn (DE); Philip Materne, Kulmain (DE); Josef Rupprecht, Erbendorf (DE)

(73) Assignee: Siemens Aktiengesellschaft, München (DE)

( * ) Notice: Subject to any disclaimer, the term of this patent is extended or adjusted under 35 U.S.C. 154(b) by 119 days.

(21) Appl. No.: 13/749,469

(22) Filed: Jan. 24, 2013

(65) Prior Publication Data

US 2013/0188780 A1    Jul. 25, 2013

(30) Foreign Application Priority Data

Jan. 25, 2012  (DE) .......................... 10 2012 201 039

(51) Int. Cl.
*G21K 1/00* (2006.01)
*G21K 1/02* (2006.01)
*A61B 6/00* (2006.01)

(52) U.S. Cl.
CPC ................ *G21K 1/00* (2013.01); *A61B 6/4291* (2013.01); *G21K 1/025* (2013.01)

(58) Field of Classification Search
CPC ........... G21K 1/00; G21K 1/025; G21K 1/10; H04N 5/32; G03B 42/00; G03B 42/04
USPC ............... 378/98.4, 98.8, 154, 155, 167, 169, 378/185, 186
See application file for complete search history.

(56) References Cited

U.S. PATENT DOCUMENTS

| | | | | | |
|---|---|---|---|---|---|
| 2,767,323 | A | * | 10/1956 | Stava et al. .................... | 378/155 |
| 3,422,542 | A | * | 1/1969 | Spurr .............................. | 33/522 |
| 3,660,660 | A | * | 5/1972 | Pearson et al. ................ | 378/155 |
| 4,105,920 | A | * | 8/1978 | Pury et al. ...................... | 378/91 |
| 4,585,350 | A | * | 4/1986 | Pryor ............................. | 356/625 |
| 4,760,589 | A |   | 7/1988 | Siczek | |

FOREIGN PATENT DOCUMENTS

GB          886935 A  *  1/1962  ............. G11B 15/22

OTHER PUBLICATIONS

German Office Action dated Oct. 9, 2012, for corresponding German Patent Application No. DE 10 2012 201 039.4 with English translation.

* cited by examiner

*Primary Examiner* — Glen Kao
*Assistant Examiner* — Julio M Duarte-Carvajali
(74) *Attorney, Agent, or Firm* — Lempia Summerfield Katz LLC

(57) ABSTRACT

An arrangement for an X-ray image system with a grid frame arranged to enable the grid frame to oscillate is provided. The arrangement includes a switch unit, with which an anti-scatter grid inserted into the grid frame may be detected. An X-ray emission is only triggered by the switch unit at a predeterminable activation time if an anti-scatter grid is inserted.

18 Claims, 2 Drawing Sheets

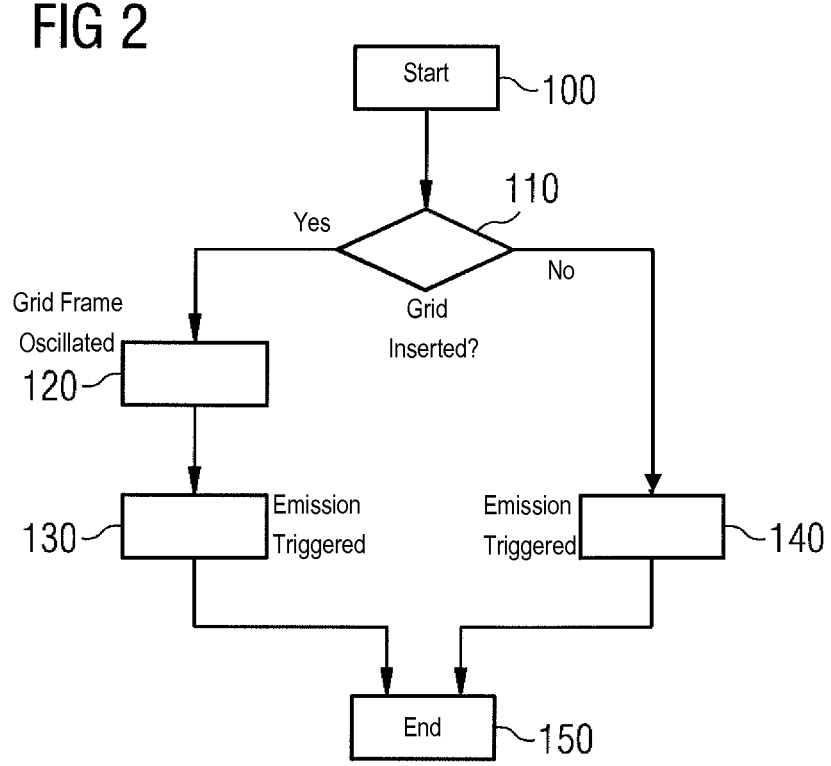

ARRANGEMENT AND METHOD FOR AN X-RAY IMAGE SYSTEM WITH A GRID FRAME ARRANGED TO ENABLE THE GRID FRAME TO OSCILLATE

This application claims the benefit of DE 10 2012 201 039.4, filed on Jan. 25, 2012, which is hereby incorporated by reference.

BACKGROUND

The present embodiments relate to an arrangement for an X-ray image system with a grid frame arranged to enable the grid fame to oscillate.

Known X-ray equipment for fluoroscopy of an object for examination has an X-ray source for the generation of X-rays that pass through the object to be X-rayed. The X-rays are recorded by an image recording device. The image recording device may be imaging cartridges for X-ray films, storage film cartridges, or X-ray image detectors for digital image recording. The image recording device is to be positioned in the X-ray beam generated by the X-ray source for this purpose. Positioning takes place by a pullout drawer, into which the image recording device is inserted and entered into a drawer housing which, for example, is integrated into a patient table of the X-ray device. There may be an automatic exposure chamber (e.g., an iontomat chamber) in the patient table above the drawer housing.

A known problem, for example, when X-raying objects for examination involving greater thickness, is scattered radiation. The scattered radiation may be formed by deflection of the examination rays in the X-rayed object for examination. An anti-scatter grid that is inserted into a grid frame above the automatic exposure chamber may be used to reduce the scattered radiation on the image recording device. For the most part, the anti-scatter grid may be removed, as X-ray images are in part taken using an anti-scatter grid with variable focus and different aspect ratios, or also in part without any anti-scatter grid.

It is known that the use of anti-scatter grids may result in distorting stripes or grids on the diagnostic image recorded in the detector. To reduce or eliminate these distorting stripes, the grid frame may be oscillated during the examination. For good image quality, the X-ray emission is to be triggered in the middle of an oscillation period of the oscillating grid frame. In known X-ray equipment, the grid frame passes through a switch, via which the time at which the X-ray emission is triggered is controlled. After expiry of a defined time (e.g., a derivative time), emission is triggered after passing through the switch. It is a proven principle to generate the oscillating grid movement by a grid frame suspended on springs. In doing so, the grid frame is preloaded with an actuator. In order to trigger the oscillating vibration, the grid frame is decoupled from the actuator. The mode of vibration results from the spring rate, the oscillating weight and the preload path. A disadvantage of this principle is that for different weights of the anti-scatter grids, different oscillation periods are set. However, as the derivative time is always the same, with anti-scatter grids of different weights, the X-ray emission may therefore not be constantly triggered in precisely the middle of an oscillation period of the oscillating grid frame.

When creating an image recording without using an anti-scatter grid, oscillation of the grid frame is to be avoided wherever possible, as these oscillations may result in image blurring. In known solutions, an additional switch is used to detect whether an anti-scatter grid is inserted in the grid frame.

SUMMARY AND DESCRIPTION

A disadvantage of the solution above is that the use of an additional switch is associated with higher production costs. The present embodiments may obviate one or more of the drawbacks or limitations in the related art. For example, these disadvantages are overcome, and an additional arrangement for an X-ray image system with a grid frame arranged to enable the grid frame to oscillate is provided.

In one embodiment, an arrangement for an X-ray image system with a grid frame arranged to enable the grid frame to oscillate is provided. The arrangement includes a switch unit, with which an anti-scatter grid inserted into the grid frame is discernible. An X-ray emission is only triggered by the switch unit at a predeterminable activation time if an anti-scatter grid is inserted. The advantage of the present embodiments is that the use of separate switches to detect an inserted anti-scatter grid and to trigger an X-ray emission is rendered unnecessary, and instead, a common switching element may be used, thus reducing the production costs of the X-ray image system.

In an embodiment, the activation time may be selected such that the X-ray emission is triggered in the middle of an oscillation period of the oscillating grid frame. In an advantageous manner, this results in a reduction of the stripes created in the X-ray image when using anti-scatter grids.

The switch unit may advantageously include a first device and a second device. The first device is arranged on the grid frame, and the second device is arranged on a pullout drawer for accommodating an image recording device. The first and second devices are operatively connected to each other.

In one embodiment, the first device may be a notched slide arranged on the grid frame. Upon insertion of an anti-scatter grid into the grid frame, the notched slide is moved from a home position in a direction of a front side of the grid frame. In this way, the notched slide is positioned as a function of the length of the inserted anti-scatter grid. This creates the precondition that even when using anti-scatter grids with different weights, the X-ray emission is triggered in the middle of an oscillation period of the oscillating grid frame. Anti-scatter grids with different weights result in different oscillation periods of the oscillating grid frame. If anti-scatter grids, in which different weights are compensated by different lengths of the anti-scatter grid are used by positioning the notched slide as a function of the length of the inserted anti-scatter grid, the X-ray emission may be triggered in the middle of an oscillation period of the oscillating grid frame, thereby increasing the quality of the X-ray image created.

In one embodiment, the arrangement may include a spring device that moves the notched slide back into the home position when the anti-scatter grid is removed from the grid frame. Repositioning the notched slide into the home position also provides that the notched slide is correctly positioned even for a subsequently inserted anti-scatter grid of a shorter length than the anti-scatter grid previously removed.

In one embodiment, the notched slide may include a switching flag with at least two notches arranged on a longitudinal side of the notched slide. When inserting the anti-scatter grid into the grid frame, the switching flag is therefore moved in the direction of the front side of the grid frame with the notched slide.

The second device may include a light barrier arranged on the pullout drawer. The use of the light barrier represents an inexpensive solution for implementing the functionality of the switch unit.

In one embodiment, the notched slide and the light barrier may be arranged in relation to each other such that the light barrier may be interrupted or released by the notches of the switching flag. The arrangement may, for example, be configured such that in an initial state with an empty grid frame, the light barrier is released by the first notch of the switching flag arranged on the notched slide. If the anti-scatter grid is inserted into the grid frame, the notched slide and the switching flag move in a direction of a front side of the grid frame at the same time, resulting in the interruption of the light barrier. The interrupted light barrier provides an indication that there is an anti-scatter grid in the grid frame that is subsequently to be oscillated for the creation of an X-ray image. An appropriate drive control provides that the first oscillation phase is also in the direction of the front side of the grid frame, as a result of which the light barrier is released via the second notch of the switching flag. This is the signal for the triggering of the X-ray emission.

An X-ray image system with one embodiment of an arrangement is also provided.

A method for generating an X-ray image using an X-ray image system is provided. A switch unit detects whether an anti-scatter grid is inserted in a grid frame arranged to enable the grid frame to oscillate. In the case of an inserted anti-scatter grid, the grid frame is oscillated, and an X-ray emission is triggered by the switch unit at a time when the oscillating grid frame is in the middle of an oscillation period. If an anti-scatter grid is not inserted, the grid frame is oscillated, and an X-ray emission is triggered independently of the oscillation state of the oscillating grid frame.

In one embodiment, a light barrier may be interrupted or released to trigger the X-ray emission. The light barrier may be arranged on a pullout drawer for accommodating an image recording device. The light barrier is interrupted and released by a switching flag including at least two notches. The switching flag is arranged on a longitudinal side of a notched slide arranged on the grid frame.

BRIEF DESCRIPTION OF THE DRAWINGS

FIG. 2 shows a flow chart of one embodiment of a method for generating an X-ray image using an X-ray image system having a switch unit.

DETAILED DESCRIPTION OF THE DRAWINGS

Figure 1:
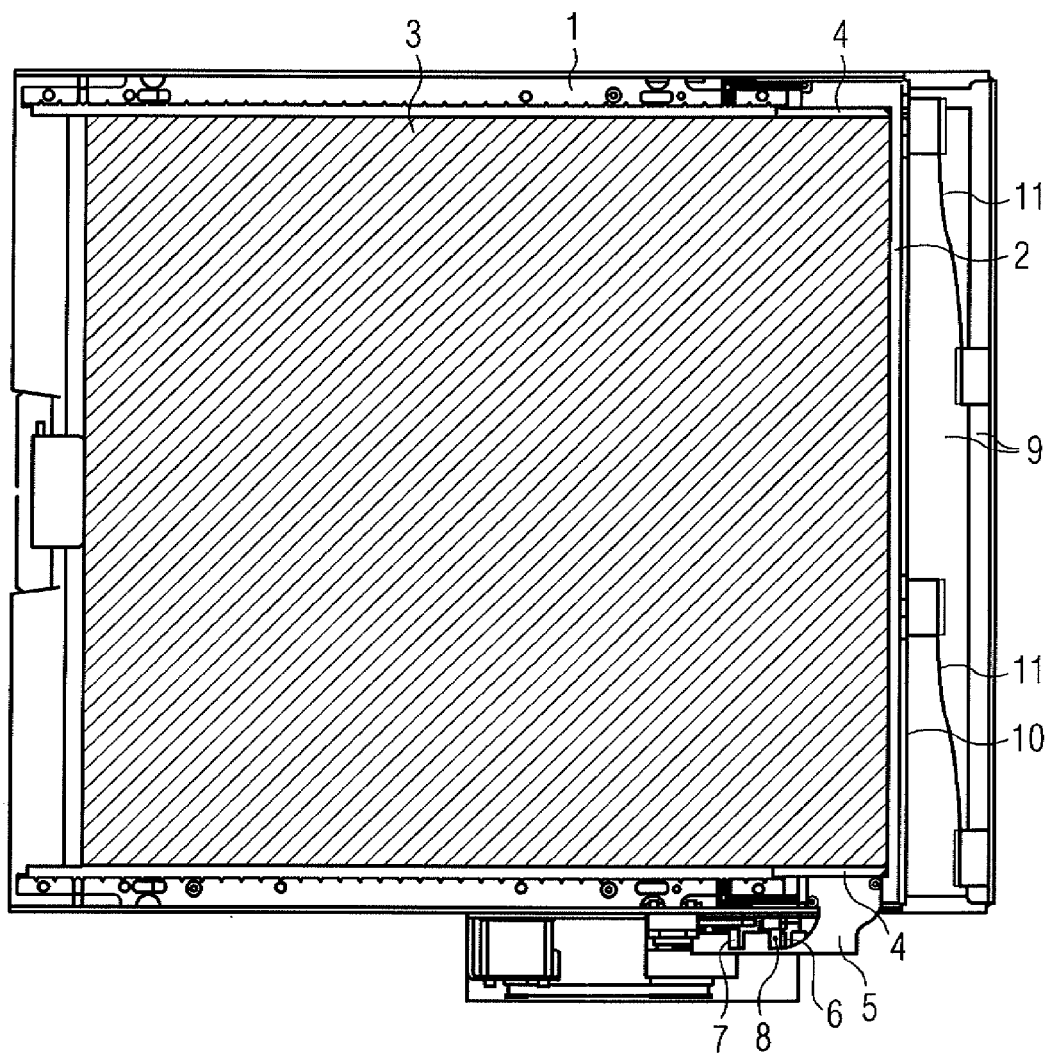
FIG. 1 shows a perspective view of one embodiment of an arrangement for an X-ray image system with a grid frame arranged to enable the grid frame to oscillate having a switch unit.

FIG. 1 shows a perspective view of one embodiment of an arrangement for an X-ray image system with a grid frame arranged to enable the grid frame to oscillate. The arrangement includes a switch unit. A grid frame 1 with a notched slide 2 is shown. An anti-scatter grid 3 is inserted into the notched slide 2. On one of two longitudinal sides 4 of the notched slide 2, a switching flag 5 that includes a first notch 6 and a second notch 7 is provided. The arrangement also includes a light barrier 8 that is arranged on a pullout drawer 9 beneath the grid frame 1. An image recording device may be inserted into the pullout drawer 9. The notched slide 2 with the switching flag 5 arranged on the one longitudinal side 4 and the light barrier 8 are arranged in relation to each other such that the light barrier 8 may be interrupted or released by the notches 6, 7 of the switching flag 5. The notched slide 2, the switching flag 5 and the light barrier 8 together form the switch unit.

In an initial state with an empty grid frame 1, the light barrier 8 is released by the first notch 6 of the switching flag 5 arranged on a longitudinal side 4 of the notched slide 2. If, as shown in FIG. 1, there is an anti-scatter grid 3 in the grid frame 1, then the notched slide 2 and the switching flag 5 move in a direction of a front side 10 of the grid frame 1 at the same time and interrupt the light barrier 8. The interrupted light barrier 8 provides an indication that there is an anti-scatter grid 3 in the grid frame 1 that is to be subsequently oscillated to create an X-ray image. A suitable drive control, which is not shown, provides that the first oscillation phase likewise takes place in a direction of the front side 10 of the grid frame 1, as a result of which the light barrier 8 is released via the second notch 7 of the switching flag 5. This is the signal for the triggering of the X-ray emission. A spring device 11, for example, in the form of leaf springs provides that the notched slide 2 is moved back into a home position when the anti-scatter grid 3 is removed from the grid frame 1. The spring device 11 includes two leaf springs 11, which are shown in FIG. 1, attached to a front side of the pullout drawer 9. On an opposite front side of the pullout drawer 9, there are two more leaf springs 11 that are not shown in FIG. 11. Repositioning the notched slide 2 into the home position also provides that the notched slide 2 is correctly positioned for a subsequently inserted anti-scatter grid 3 of a shorter length than the anti-scatter grid 3 previously removed. This provides that the specific length of an inserted anti-scatter grid 3 is taken into account to the effect that the X-ray emission is triggered as a function of the length of the inserted anti-scatter grid 3.

FIG. 2 shows a flow chart of one embodiment of a method for generating an X-ray image using an X-ray image system having a switch unit. In act 100, the method is started. In act 110, a switch unit checks and detects whether an anti-scatter grid is inserted in a grid frame arranged to enable the grid frame to oscillate. In the case of an inserted anti-scatter grid, in act 120, the grid frame is oscillated. In act 130, an X-ray emission is triggered by the switch unit at a time at which the oscillating grid frame is in the middle of an oscillation cycle. Subsequently, the method is terminated in act 150. If an anti-scatter grid is not inserted, an X-ray emission is triggered in the act 140 regardless of the oscillation state of the oscillating grid frame, and subsequently, the method is terminated in act 150.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An arrangement for an X-ray image system with a grid frame arranged to enable the grid frame to oscillate, the arrangement comprising:
   a switch unit, with which an anti-scatter grid inserted into the grid frame is detectable, and using which, in the case of the inserted anti-scatter grid, an X-ray emission is triggerable at a predeterminable activation time,
   wherein the switch unit comprises a notched slide arranged on the grid frame, the notched slide being moved from a home position in a direction of a front side of the grid frame when the anti-scatter grid is inserted.

2. The arrangement as claimed in claim 1, wherein the predeterminable activation time is selectable such that the X-ray emission is triggered in the middle of an oscillation period of the oscillating grid frame.

3. The arrangement as claimed in claim 2, wherein the switch unit comprises:
   a first device comprising the notched slide; and
   a second device,
   wherein the first device is arranged on the grid frame, and the second device is arranged on a pullout drawer for accommodating an image recording device, and
   wherein the first device and the second device are operatively connected to each other.

4. The arrangement as claimed in claim 1, wherein the switch unit comprises:
   a first device comprising the notched slide; and
   a second device,
   wherein the first device is arranged on the grid frame, and the second device is arranged on a pullout drawer for accommodating an image recording device, and
   wherein the first device and the second device are operatively connected to each other.

5. The arrangement as claimed in claim 4, wherein the notched slide comprises a switching flag having at least two notches arranged on a longitudinal side of the notched slide.

6. The arrangement as claimed in claim 5, wherein the second device comprises a light barrier arranged on the pullout drawer.

7. The arrangement as claimed in claim 6, wherein the notched slide and the light barrier are arranged in relation to each other such that the light barrier is interruptible or releasable by the at least two notches of the switching flag.

8. The arrangement as claimed in claim 1, further comprising a spring device that moves the notched slide back into the home position when the anti-scatter grid is removed from the grid frame.

9. The arrangement as claimed in claim 8, wherein the notched slide comprises a switching flag having at least two notches arranged on a longitudinal side of the notched slide.

10. An X-ray image system comprising:
    a grid frame arranged to enable the grid frame to oscillate; and
    an arrangement comprising:
      a switch unit, with which an anti-scatter grid inserted into the grid frame is detectable, and using which, in the case of the inserted anti-scatter grid, an X-ray emission is triggerable at a predeterminable activation time,
    wherein the switch unit comprises a notched slide arranged on the grid frame, the notched slide being moved from a home position in a direction of a front side of the grid frame when the anti-scatter grid is inserted.

11. The X-ray image system as claimed in claim 10, wherein the predeterminable activation time is selectable such that the X-ray emission is triggered in the middle of an oscillation period of the oscillating grid frame.

12. The X-ray image system as claimed in claim 10, wherein the switch unit comprises:
    a first device comprising the notched slide; and
    a second device,
    wherein the first device is arranged on the grid frame, and the second device is arranged on a pullout drawer for accommodating an image recording device, and
    wherein the first device and the second device are operatively connected to each other.

13. The X-ray image system as claimed in claim 12, wherein the notched slide comprises a switching flag having at least two notches arranged on a longitudinal side of the notched slide.

14. The X-ray image system as claimed in claim 13, wherein the second device comprises a light barrier arranged on the pullout drawer.

15. The X-ray image system as claimed in claim 14, wherein the notched slide and the light barrier are arranged in relation to each other such that the light barrier is interruptible or releasable by the at least two notches of the switching flag.

16. The X-ray image system as claimed in claim 10, further comprising a spring device that moves the notched slide back into the home position when the anti-scatter grid is removed from the grid frame.

17. A method for generating an X-ray image using an X-ray image system, the method comprising:
    detecting, by a switch unit, whether an anti-scatter grid is inserted in a grid frame arranged to enable the grid frame to oscillate, the switch unit comprising a notched slide arranged on the grid frame, the notched slide being movable from a home position in a direction of a front side of the grid frame when the anti-scatter grid is inserted;
    oscillating the grid frame and triggering an X-ray emission by the switch unit at a time, at which the oscillating grid frame is in the middle of an oscillation period, in the case of an inserted anti-scatter grid; and
    oscillating the grid frame and triggering the X-ray emission regardless of an oscillation state of the oscillating grid frame when the anti-scatter grid is not inserted.

18. The method as claimed in claim 17, further comprising interrupting or releasing a light barrier to trigger the X-ray emission, wherein the light barrier is arranged on a pullout drawer for accommodating an image recording device using a switching flag comprising at least two notches, the switching flag being arranged on a longitudinal side of a notched slide arranged on the grid frame.

* * * * *